United States Patent [19]

Epstein

[11] Patent Number: 4,713,484
[45] Date of Patent: Dec. 15, 1987

[54] SINGLE PHASE CARBONYLATION OF AROMATIC HALIDES TO CARBOXYLIC ACID SALTS

[75] Inventor: Ronald A. Epstein, Yonkers, N.Y.

[73] Assignee: Stauffer Chemical Company, Westport, Conn.

[21] Appl. No.: 945,257

[22] Filed: Dec. 22, 1986

Related U.S. Application Data

[63] Continuation-in-part of Ser. No. 796,687, Nov. 12, 1985.

[51] Int. Cl.[4] .............................................. C07C 51/14
[52] U.S. Cl. .................................... 562/406; 562/520; 560/105
[58] Field of Search ................................ 562/406, 520

[56] References Cited

U.S. PATENT DOCUMENTS

| | | | |
|---|---|---|---|
| 3,991,101 | 11/1976 | Knifton | 562/520 |
| 4,034,004 | 7/1977 | Cassar | 562/406 |
| 4,102,921 | 7/1978 | Bartish | 562/520 |
| 4,582,929 | 4/1986 | De Vries | 562/520 |

Primary Examiner—Paul J. Killos
Attorney, Agent, or Firm—Vivienne T. White

[57] ABSTRACT

A process for preparing carboxylic acid salts by the reaction of carbon monoxide with substituted or unsubstituted aromatic halides or an aliphatic organic halide. The process comprises the catalytic single phase carbonylation of the halide utilizing in addition to carbon monoxide, a palladium catalyst, an excess of tertiary phosphine, optionally an amine compound, with an alkali metal or alkaline earth metal base added during the reaction to form the salt.

29 Claims, No Drawings

SINGLE PHASE CARBONYLATION OF AROMATIC HALIDES TO CARBOXYLIC ACID SALTS

CROSS REFERENCE TO RELATED APPLICATIONS

This application is a continuation-in-part of copending application Ser. No. 796,687 filed Nov. 12, 1985.

BACKGROUND OF THE INVENTION

The present invention relates to the process for preparing carboxylic acid salts starting from organic halides. More particularly, this invention relates to the single phase carbonylation of organic halides by the reaction of such halides with carbon monoxide catalyzed by complexes of palladium and utilized with an excess of phosphine in the reaction.

The compounds thus obtained have important industrial applications. Their acids may be used in various technological fields such as, for instance, in the preparation of cosmetic products (perfumes from benzoic and phenylacetic acids, etc.), products from agriculture (3,5-dichloro-N-(1,1-dimethyl)-2-propenyl benzamide; Cidial etc.), of dye stuffs and pigments (naphthoic acid), of plasticizers (terephthalic acid), etc.

It is known to carbonylate halohydrocarbons such as benzyl chloride by the reaction of carbon monoxide and alcohol at 100° C. or below and at atmospheric pressures in the presence of an amine and a catalytic amount of a palladium catalyst to form esters. U.S. Pat. No. 3,116,306 discloses a process for preparing carboxylated organic compounds such as acids by reacting (1) an organic compound represented by the general formula $R_nZ$ in which R is an organic compound having at least one aliphatic radial or cycloaliphatic radial, Z is $SO_4$, X, $X_2$ or $R'SO_3$, X being a halogen and R' is alkyl, alkenyl, cycloaklyl, aryl or arylalkyl where N is 1, Z is X, $X_2$ or $R'SO_3$ and where N is 2, Z is $SO_4$, the Z substituent being attached to an aliphatic or a cycloaliphatic primary or secondary carbon atom;

(2) carbon monoxide;

(3) a salt of a metal hydrocarbonyl of the group consisting of cobalt hydrotetracarbonyl and iron dihydrotetracarbonyl; and (4) a material of the group consisting of water, alcohols, phenols, mercaptans, ammonia, hydrazine, primary organo-nitrogen bases and secondary organo-nitrogen bases.

U.S. Pat. No. 4,034,004 discloses a process for the preparation of carboxylic acids from organic halides. The disclosed process comprises the reaction of aromatic or aliphatic organic halides with carbon monoxide utilizing a phosphinic palladium complex catalyst in the presence of a quaternary alkyl ammonium salt wherein the process is conducted in a double liquid phase consisting essentially of the organic halide and catalytic palladium complex and an aqueous inorganic alkaline solution containing the quaternary alkyl ammonium salt.

Unlike the present single phase system disclosed in the instant application, the above reference discloses a two-phase system. In addition, the reference teaches the use of a solvent that is immiscible in $H_2O$.

SUMMARY OF THE INVENTION

The present invention comprises a single phase palladium catalyzed carbonylation of halocarbons to form carboxylic acid salts under mild conditions. The process of the invention is the carbonylation of halocarbons in the presence of a palladium catalyst with tertiary phosphine ligands used in excess, the salt being formed by the reaction with an alkali metal or alkaline earth base, and wherein the base and excess phosphine are added during the reaction at a rate necessary to maximize product yield. The process of the invention further comprises the use of a hindered amine compound.

DETAILED DESCRIPTION OF THE INVENTION

The instant process comprises the carbonylation of an organic halide compound, having the formula RX, in the presence of an alcohol, a palladium catalyst combined with a tertiary phosphine used in an excess amount, optionally, a hindered amine base, and an alkali metal or alkaline earth metal base. In the instant specification the abbreviation "Ph" is meant to indicate a phenyl moiety.

In general, the optional hindered amine compound is one having at least two branched aliphatic or cycloaliphatic groups or one in which the N atom is in a cycloaliphatic or aromatic ring, substituted in a manner that induces steric crowding around the N atom. Primary and secondary amines can react with the carbonylated intermediate to form an amide. Generally such compounds comprises the formula $R'_3N$ wherein R' can comprise a branched $C_3$–$C_{10}$ aliphatic constituent or combinations of branched aliphatic and straight chained aliphatic compounds having from 1–10 carbon atoms, a cyclic compound or an aromatic compound, or combinations of the above.

An example of the present invention is the reaction:

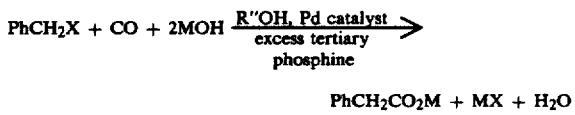

$$PhCH_2X + CO + 2MOH \xrightarrow[\text{excess tertiary phosphine}]{R''OH, Pd \text{ catalyst}}$$

$$PhCH_2CO_2M + MX + H_2O$$

wherein R" is an alkyl of from $C_1$ to $C_{10}$, cycloalkyl, aryl, or aralkyl group; X is a halogen and M is an alkali or alkaline earth metal.

Alkali and alkaline earth metal bases used in the process can comprise lithium, sodium, potassium, magnesium, or calcium hydroxides or oxides. If an amine base is used, at least one mole equivalent of metal base is needed per mole of halocarbon, with additional amounts used depending upon the quantity of amine used.

For the purposes of this invention, the symbol R in the formula RX may be ethylenically unsaturated aliphatic radicals such as ethenyl, methallyl, butenyl, pentenyl, undecenyl, allyloxymethyl, methyallyloxymethyl, and the like; cycloaliphatic; aliphatic substituted or unsubstituted aralkyl radicals such as benzyl, phenethyl, phenylpropyl, phenylallyl, p-vinylbenzyl, phenylisopropyl, phenyloctyl, methoxylbenzyl, xylyl, alpha-methylnaphthyl, beta-methylnaphthyl, and the like; or heterocyclic radicals such as methylene thiophene, dimethylene thiophene, and the like.

It has been found that organic halides suitable for the purposes of this invention are monohalogen and dihalogen, substituted or unsubstituted organic compounds having at least one aliphatic or cycloaliphatic radical within the molecule and in which the halogen is attached to primary or secondary carbon atoms within said aliphatic or cycloaliphatic radicals. By way of example, but not in limitation of the invention, suitable organic halides include alkenyl halides, such as allyl chloride, allyl bromide, methallyl chloride, pentenyl chloride, pentenyl iodide, undecenyl chloride, dichloropentene, and the like; aralkyl halides, such as benzyl chloride, ortho-, meta- and paramethoxy benzyl chlorides, alpha-monochloro-xylene and alpha, alpha-dichloro-xylene (ortho, meta or para), alpha-chloromethylnaphthalene, beta-chloromethylnaphthalene, alpha-chloromesitylene, benzyl bromide, benzyl iodide, veratryl chloride, alpha-iodoxylene (ortho, meta or para), methyl p-chloromethylbenzoate, and the like; and heterocyclic halides, such as chloromethylthiophene, and the like.

Catalysts for practicing the invention are derived from palladium (II) complexes exemplified by the general formula $PdX_2L_2$ where X=halide and L=tertiary phosphine or a group such as benzonitrile which will exchange with tertiary phosphine in solution, or $PdX_4^{2-}$ or $PdCl_2$ which will react with tertiary phosphine to yield $PdX_2L_2$; or palladium (O) complexes exemplified by (1) $PdL_n$ where L=tertiary phosphine and n=2-4, or L=dibenzylidene acetone and n=2 (which will react with tertiary phosphine in solution), (2) $Pd_x(CO)_yL_z$ where L=tertiary phosphine, x=y=1 and z=3 or x=y=3, z=3 or 4. These complexes may be prepared in situ or prior to being added to the reaction.

It has been found that suitable catalysts include $PdCl_2(PPh_3)_2$, $PdCl_2(PhC\equiv N)_2$, and $PdCl_2(CH_3C\equiv N)_2$. The moiety ($PPh_3$) is triphenyl phosphine.

An excess of phosphine is used in the process over that generally supplied in the formulae $PdX_2L_2$ or $Pd_x(CO)_yL_z$ which has a ratio of phosphine to palladium of from about 1:1 to 3:1, depending on the specific complex used. The molar ratio of the excess phosphine to Pd used should be from about 2:1 to about 100:1 and preferably from about 3:1 to about 30:1. Since the ratios given are molar ratios they would be the same if expressed as the ratio of P:Pd or $PPh_3$:Pd. Most desirably, the molar ratio of phosphine to Pd should be 5:1 to 15:1. Suitable compounds for supplying excess phosphine are the tertiary phosphines and include compounds of the formula $PR^1R^2R^3$ where $R^1$, $R_2$ and $R^3$ are phenyl or substituted phenyl groups such as ortho, meta or para tolyl, methoxy phenyl or phenyl ethyl groups.

The amount of catalyst utilized in the process ranges from about 0.01 mole % of the halohydrocarbon to about 10 mole % and preferably from about 0.02 mole % to about 0.6 mole %.

An excess of carbon monoxide over theoretical stoichiometric requirements is utilized in the process. Preferably a large excess of carbon monoxide is employed and the reaction is usually and conveniently carried out in an atmosphere of carbon monoxide. However, pure carbon monoxide need not necessarily be used in this reaction and mixtures of carbon monoxide with such gases as nitrogen, argon, methane, ethane, and the like, which are inert with respect to the carbonylation reaction, are entirely satisfactory for the purposes of this invention.

A wide range of pressure has been found suitable for the purposes of this invention, from about atmospheric or less to about 351.54 Kg/sq.cm (5,000 lbs/in$^2$) or more. Pressures from about atmospheric and about 35.15 Kg/sq.cm (500 lbs/in$^2$) are desirable while from atmospheric to about 100 lbs/in$^2$ (7.03 Kg/cm$^2$) are most preferred. Similarly, the process of this invention can be carried out within a wide range of temperatures, from about 0° C. to about 150° C. or even higher. Preferred temperatures are from about 50° C. to about 100° C. The formation of some esters are more rapid as compared to other esters. As such, the preferred process temperature necessary for preparing the various esters may vary considerably.

A hydrogen halide acceptor is used to make the carbonylation process catalytic. In its absence free hydrogen halide is not formed. The optionally added amine or the alkali metal or alkaline earth base function as hydrogen halide acceptors. When an amine is used as a hydrogen halide acceptor, an amine hydrogen halide salt is formed and generally subsequently neutralized by the alkali or alkaline earth base, depending on the base used. The metal halide salt is formed when an alkali metal or alkaline earth base is used. Suitable amines are represented by any hindered amine base such as, for instance, diisopropylethyl amine, diisopropyl methyl amine and dicyclohexyl ethyl amine are suitable for use in the practice of the invention.

Typical alcohols suitable for the purposes of this invention include aliphatic alcohols such as methyl alcohol, ethyl alcohol, propyl alcohol, isopropyl alcohol, n-butyl alcohol, secondary butyl alcohol, n-hexyl-alcohol, hexanol-2, n-octyl alcohol, capryl alcohol, isopropyl dodecyl alcohol, stearyl alcohol, ceryl alcohol, myricyl alcohol, and the like; polyhydric compounds such as ethylene glycol, diethylene glycol, glycerol, and the like; olefinic alcohols such as crotyl alcohol, buten-1-ol-4, penten-1-ol-5, 2,6-dimethylocten-1-ol-8, and the like; cycloaliphatic alcohols such as cyclopentyl alcohol, cyclohexyl alcohol, methyl cyclohexyl alcohol, and the like; aralkyl alcohols such as benzyl alcohol, diphenylcarbinol, phenylethyl alcohol, phenyl propyl alcohol, cinnamyl alcohol, and the like.

The instant invention can be practiced in the presence of water, since the solvent is miscible with water, and since water is produced during the reaction. Practicing the invention under initially anhydrous conditions is also desirable.

The alkali or alkaline earth metal base is utilized to produce the salt of the acid. The alkali metal hydroxide is used in the process of the invention in an amount of 1 to 4 and preferably in an amount of 2 to 3 moles per mole of the organic halide use. The normal stoichiometry for the process is 1:1:2 of halocarbon to CO to alkali or alkaline earth base.

In the practice of the invention, the base is added separately to the organic halide during the reaction process, preferably with the addition of the excess tertiary phosphine. It was found, as shown in the comparative examples provided, that addition of the base prior to reaction results in minor conversion to the product salt with the formation of ether. The reaction of the organic halide with the base is faster than the catalyzed carbonylation process. It is, therefore, necessary to meter the base to the reactor containing the organic halide and catalyst during the reaction. To prevent formation of byproduct ethers, it is necessary to control the rate of addition of the base. Too fast an addition results in formation of the by-product. The specific rate can be easily determined for all process conditions.

It is also a process requirement to add excess tertiary phosphine to the reactor during the process to prevent the catalyst from precipitating and thereby losing its activity. Comparative Example 2 illustrates this.

In the process of the invention, only an organic phase is present during the reaction. Water formed during the process dissolves in the alcohol.

In an embodiment of the invention a reactor is charged with catalyst containing phosphine, organic halide, alcohol and optionally a hindered amine compound. Separately, a solution of alkali metal hydroxide and alcohol is prepared as well as a solution of phosphine in alcohol. Optionally, single solution containing base and phosphine may be used. A slurry of base in alcohol and a phosphine slurry in alcohol or solids thereof can also be used which would decrese the amount of alcohol used. The reactor is heated to a temperature of from about 50° C. to about 100° C. and the alkali metal hydroxide and phosphine solutions are charged into the reactor with additional amounts of carbon monoxide. The reaction is continued for a time sufficient to produce the alkali metal salt of the carboxylic acid.

The following examples are descriptive of the process of the invention.

EXAMPLE 1

Into a (350 ml) glass reactor equipped with a mechanical stirrer, gas inlet and outlet, thermocouple, and liquid addition tubes, was placed 52.9 mg $PdCl_2(PPh_3)_2$ and 0.189 g $PPh_3$. The reactor was sealed, evacuated, and filled with $N_2$. Under a $N_2$ purge, deoxygenated benzyl chloride, 16.81 g, methanol, 59.2 g, and diisopropyl ethyl amine, 0.26 g, were added.

In a Schlenk flask, a methanol solution of KOH was prepared under an inert atmosphere from 20.15 g KOH (87.8%), and 54.3 g methanol. In a second Schlenk flask 0.331 g $PPh_3$ was dissolved in 30.7 g of deoxygenerated methanol under $N_2$.

The reactor was flushed with high purity CO, pressurized to 15 psig and heating begun. When the temperature reached 80° C. addition of the KOH and $PPh_3$ solutions was started using a pair of metering pumps. With a stirring rate of 800 rpm, the pressure was increased to and maintained at 45 psig by feeding CO on demand. The temperature was kept at 80° C. for 100 minutes. The reactor was then cooled and vented. 52 ml of the KOH solution and 22.8 ml of the $PPh_3$ solution was added during the reaction.

LC and GC analysis of reaction product revealed a 100% conversion of benzyl chloride with a 63% yield of potassium phenylacetate, and a 28% yield of methyl phenylacetate. An overall yield of carbonylated products of 91% was therefore achieved.

The amount of KOH used in this reaction (~224 mmole) was ~84% of the stoichiometric amount required. If sufficient KOH had been added, the methyl phenylacetate produced would have been hydrolyzed to potassium phenylacetate giving a 91% yield of potassium phenylacetate.

EXAMPLE 2

A carbonylation was performed using the same equipment and procedures as in Example 1. 51.9 mg $PdCl_2(PPh_3)_2$, 0.191 g $PPh_3$, 15.6 g benzyl chloride, and 61.3 g methanol were added to the reactor. 20.2 g KOH (87.7%) and 52.9 g methanol were used to prepare the KOH solution, and 0.333 g $PPh_3$ was dissolved in 28.9 g methanol to prepare the triphenyl phosphine solution.

The carbonyltion was run for 90 minutes during which time 63 ml of the KOH solution, and 21 ml of the $PPh_3$ solution were added. An 86% overall yield of potassium phenylacetate was obtained.

EXAMPLE 3

The following amounts of reagents were used in a carbonylation as described in Example 1:

Reactor: 50.1 mg $PdCl_2(PPh_3)_2$; 0.191 g $PPh_3$; 16.14 g benzyl chloride; 60.5 g methanol.
KOH solution: 20.2 g KOH (87.8%); 53.5 g methanol.
$PPh_3$ solution: 0.333 g $PPh_3$; 29.9 g methanol.

Under the conditions outlined above, 65 ml of the KOH solution, and 22 ml of the triphenyl phosphine solution were added to the reactor over a one hour and 37-minute period. The reaction was maintained at 80° C. for an additional 24 minutes. A 100% conversion of the benzyl chloride with a 85% yield of potassium phenylacetate was obtained.

EXAMPLE 4

To the same reactor as described in Example 1 were charged 50.6 mg $PdCl_2(PPh_3)_2$, 0.558 g $PPh_3$, and 59.6 g methanol. In a Schlenk flask a solution was prepared from 57.9 g KOH (87.8%) and 142.3 g methanol. In a second Schlenk flask was placed 69.9 g of benzyl chloride.

With the solution in the reactor at 80° C., 45 psig CO, with stirring at 800 rpm, the addition of benzyl chloride at 0.49 ml/min was started. Ten seconds later the KOH addition was begun at 1.34 ml/min. After 1 hour and 30 minutes, the benzyl chloride addition was stopped. The KOH was fed into the reactor for another 35 minutes after which the reaction was maintained under operating conditions for an additional 25 minutes.

During the reaction 46.6 ml of benzyl chloride and 165.8 ml of the KOH solution were added. Analysis of the reaction product revealed that a 99% conversion was obtained with a 70% yield of potassium phenylacetate.

EXAMPLE 5

Using the procedure described in Example 1, a carbonylation was run with the following reagents:

Reactor: 50.1 mg $PdCl_2(PPh_3)_2$; 0.193 g $PPh_3$; 17.69 g benzyl chloride; 60.3 g methanol.
KOH solution: 20.2 g KOH (87.8%); 53.7 g methanol.
$PPh_3$ solution: 0.333 g $PPh_3$; 29.8 g methanol.

Under the described reaction conditions, 56.5 g KOH solution and 14.2 g $PPh_3$ solution were added to the reactor at a constant rate over 38 minutes. The system was maintained under reaction conditions for an additional five minutes, cooled, and then vented.

A nearly quantitative conversion of the benzyl chloride was obtained. The yield of carbonylated product was 93% which consisted of a 68% yield of potassium phenylacetate and a 25% yield of methyl phenylacetate. The amount of KOH used in this reaction (~243 mmole) was ~87% of the stiochiometric amount required. Had additional KOH been added, the methyl phenylacetate would have been converted to potassium phenylacetate for a yield of 93%.

EXAMPLE 6

The carbonylation reaction was set up using the following components:

Reactor: 101.7 mg $PdCl_2(PPh_3)_2$; 0.386 g $PPh_3$; 17.94 g benzyl chloride; 62.7 g methanol.
KOH solution: 20.3 g KOH (87.8%); 53.5 g methanol.
$PPh_3$ solution: 0.660 g $PPh_3$; 30.2 g methanol.

The reaction was run at 80° C., 45 psig, with a stirring rate of 800 rpm. 62 ml of the KOH and 18 ml of the $PPh_3$ solutions were added over 44 minutes. After five additional minutes, the reactor was cooled and vented. A 100% conversion and a 97% overall yield to carbonylated product was found (82% potassium phenylacetate and 15% methyl phenylacetate). 94% of the required KOH was added.

EXAMPLE 7

This reaction was run using a mixed methanol/isopropanol reaction medium using the apparatus described in Example 1.

Reactor: 100.1 mg $PdCl_2(PPh_3)_2$; 0.386 g $PPh_3$; 17.66 g benzyl chloride; 11.27 g methanol; 53.0 g isopropanol.
KOH solution: 20.2 g KOH (87.8%); 53.0 g methanol.
$PPh_3$ solution: 0.664 g $PPh_3$; 29.2 g isopropanol.

Under the reaction conditions described in Example 1, 64 ml KOH and 19.2 ml $PPh_3$ were added over 43 min. After five more minutes, the reactor was cooled and vented. A 92% yield of potassium phenylacetate and 4% methyl phenylacetate was obtained on a nearly quantitative conversion. 98% of the stiochiometric amount of KOH was added.

EXAMPLE 8

A carbonylation reaction was set up without using anaerobic procedures, as previously used in the other Examples.

Reactor: 50.7 mg $PdCl_2 PPh_3)_2$; 0.222 g $PPh_3$; 16.00 g benzyl chloride; 61.1 g methanol.
KOH solution: 20.2 g KOH (87.8%); 52.6 g methanol.
$PPh_3$ solution: 0.331 g $PPh_3$; 29.5 g methanol.

After establishing operating temperature and pressure in the reactor, 59 ml of the KOH solution and 19 ml of the $PPh_3$ solution were added over 17 minutes. The reactor was maintained at reaction conditions for five more minutes, then cooled and vented. An 85% yield of potassium phenylacetate was found with a quantitative conversion of starting material.

EXAMPLE 9

As in Example 8, the following materials were used:
Reactor: 50.0 mg $PdCl_2(PPh_3)_2$; 0.202 g $PPh_3$; 33.73 g benzyl chloride; 4.7 g methanol.
KOH solution: 40.4 g KOH (87.8%); 106.1 g methanol.
$PPh_3$ solution: 0.667 g $PPh_3$; 56.2 g methanol.

Under the reaction conditions described in Example 1, 128 ml of the KOH solution, and 19.4 ml of the $PPh_3$ solution were delivered to the reactor over a 45-minute period. After five additional minutes, the reactor was cooled and vented.

LC and GC analyses revealed that a 94% yield of potassium phenylacetate was obtained on a 97% conversion.

COMPARATIVE EXAMPLE 1

Into the same reactor described in Example 1 was placed 53.7 mg $PdCl_2(PPh_3)_2$, 0.285 g $PPh_3$, and 17.45 g KOH (87.8%). Under a $N_2$ purge, deoxygenated benzyl chloride, 17.86 g methanol, 81.7 g, and diisopropyl ethyl amine, 0.23 g, were added. The reactor was flushed with high purity CO, pressurized to 15 psig, and heating begun with stirring.

At 79° the pressure was increased from 26 to 45 psig and maintained at this value during the reaction. After 1 hr. 40 min. under these conditions, the heating has stopped and the reactor vented when cool.

Analysis of the reaction product revealed that only at 6% conversion to potassium phenylacetate was obtained. The remaining benzyl chloride was converted to benzyl methyl ether. This experiment shows that the reaction of benzyl chloride with methanol and KOH is faster than the catalyzed carbonylation. It demonstrates the need to meter the KOH into the benzyl chloride/methanol/catalyst solution during the reaction.

COMPARATIVE EXAMPLE 2

The reactor and one Schlenk flask were charged as follows:

Reactor: 52.1 mg $PdCl_2(PPh_3)_2$; 0.193 g $PPh_3$; 16.23 g benzyl chloride; 60.1 g methanol.
KOH solution: 20.2 g KOH (87.8%); 70.5 g methanol.

Under the reaction conditions specified in Example 1, 84 ml of the KOH solution was added over 1 hr. 27 min. After an additional 20 minutes at temperature, the system was cooled and vented.

A 41% yield of potassium phenylacetate with a quantitative conversion of the benzyl chloride was obtained. 53% of the benzyl chloride was converted to benzyl methyl ether in an uncatalyzed side reaction. The relatively low yield of potassium phenylacetate and the large quantity of ether indicates that the catalyst suffers a loss activity in the absence of the added $PPh_3$.

What is claimed is:

1. A process for preparing carboxylic acid salts comprising the single phase carbonylation of at least one organic halide in the presence of an alcohol, CO, and a base in conjunction with a palladium catalyst and an excess of tertiary phosphine, and wherein the base and excess phosphine is added during the reaction at a rate necessary to prevent side-product formation and catalyst decay.

2. The process of claim 1 further comprising the use of a hindered amine compound.

3. The process of claim 2 wherein the amine compound is a tertiary hindered amine base of the formula $R'_3N$, wherein R' comprises $C_3$–$C_{10}$ branched aliphatic compounds, cyclic compounds and aromatic compounds or mixtures of the above.

4. The process of claim 3 wherein the tertiary hindered amine base is N,N-diisopropylethyl amine.

5. The process of claim 3 wherein the tertiary hindered amine base is N,N-diisopropylmethyl amine.

6. The process of claim 3 wherein the tertiary hindered amine base is dicyclohexyl ethyl amine.

7. The process of claim 1 wherein the base is an alkali metal hydroxide or oxide.

8. The process of claim 7 wherein the base is potassium hydroxide.

9. The process of claim 1 wherein the base is an alkaline earth hydroxide or oxide.

10. The process of claim 1 wherein the excess tertiary phosphine is added in the form of triphenyl phosphine.

11. The process of claim 1 wherein the catalyst is a palladium II complex having the formula $PdX_2L_2$, where X is a halide and L is a tertiary phosphine.

12. The process of claim 11 wherein the palladium catalyst is $PdCl_2(PPh_3)_2$.

13. The process of claim 11 wherein L is a benzonitrile.

14. The process of claim 1 wherein the halocarbon is benzyl chloride.

15. The process of claim 13 wherein the benzonitrile reacts with phosphine in situ.

16. The process of claim 1 wherein the alcohol is isopropanol.

17. The process of claim 1 wherein the alcohol is methanol.

18. The process of claim 1 conducted under anhydrous conditions.

19. The process of claim 1 wherein the excess phosphine to palladium ratio is above about 2:1 to 100:1.

20. The process of claim 15 wherein the excess phosphine to palladium ratio is from about 3:1 to 30:1.

21. The process of claim 16 wherein the excess phosphine to palladium ratio is from about 5:1 to 15:1.

22. The process of claim 1 wherein the base is used in a molar ratio of from about 1 to about 4 per mole of the halocarbon.

23. The process of claim 22 wherein the base is used in a molar ratio of from about 2 to about 3 mole per mole of the halocarbon.

24. The process of claim 1 wherein the base and phosphine is added at a rate sufficient to prevent precipitation of the catalyst.

25. The process of claim 1 wherein the base is added at a rate sufficient to prevent formation of by-product ethers.

26. The process of claim 1 wherein the organic halide is benzyl chloride.

27. The process of claim 1 wherein the reaction is conducted at from atmospheric pressure to pressures of about 351.54 Kg/cm.

28. The process of claim 1 wherein the reaction is conducted at temperatures of from about 0° C. to about 150° C.

29. The process of claim 28 wherein the reaction is conducted at temperatures of from about 50° C. to about 100° C.

* * * * *

UNITED STATES PATENT AND TRADEMARK OFFICE
CERTIFICATE OF CORRECTION

PATENT NO. : 4,713,484
DATED : December 15, 1987
INVENTOR(S) : Ronald A. Epstein It is certified that error appears in the above-identified patent and that said Letters Patent is hereby corrected as shown below:

Col. 2, line 32, "comprises" should be -- comprise --;

Col. 3, line 41, "$Pd_x(CO)_yL_z$" should be -- $Pd_x \cdot (CO)_yL_z$ --;

Col. 3, line 51, "$R_2$" should be -- $R^2$ --;

Col. 5, line 18, "decrese" should be -- decrease --;

Col. 5, line 52, "analysis" should be -- analyses --;

Col. 6, line 4, "carbonyltion" should be -- carbonylation --;

Col. 7, line 41, "$PdCl_2PPh_3)_2$" should be -- $PdCl_2(PPh_3)_2$ --; and

Col. 8, line 40, "loss activity" should be -- loss of activity --.

Signed and Sealed this

Twenty-eighth Day of June, 1988

Attest:

DONALD J. QUIGG

Attesting Officer

Commissioner of Patents and Trademarks